United States Patent [19]

Kenig et al.

[11] Patent Number: 5,674,869
[45] Date of Patent: Oct. 7, 1997

[54] PHARMACEUTICAL TREATMENT

[75] Inventors: Martin David John Kenig; Richard Anthony Vere Hodge, both of Epsom, England

[73] Assignee: Beecham Group plc, Brentford, United Kingdom

[21] Appl. No.: 469,273

[22] Filed: Jun. 6, 1995

Related U.S. Application Data

[63] Continuation of Ser. No. 380,226, Jan. 27, 1995, abandoned, which is a continuation of Ser. No. 237,936, May 2, 1994, abandoned, which is a continuation of Ser. No. 971,917, Jan. 28, 1993, abandoned.

[30] Foreign Application Priority Data

Jul. 7, 1990 [GB] United Kingdom ............... 9015051

[51] Int. Cl.$^6$ ................................................ A61K 31/52
[52] U.S. Cl. ............................................................ 514/262
[58] Field of Search ................................................ 514/262

[56] References Cited

U.S. PATENT DOCUMENTS

| 4,798,833 | 1/1989 | Johansson et al. | 514/262 |
| 4,942,166 | 7/1990 | Harnden et al. | 514/262 |
| 5,075,445 | 12/1991 | Jarvest et al. | 544/276 |

OTHER PUBLICATIONS

Heng et al., Lancet, 343, pp. 255–258 (1994).
Monitor Weekly, vol. 7, Mar. 16, 1994, p. 29.
Hodge et al 112 CA:83948u 1990.
Harnden et al 107 CA: 97051f 1987.
Harnden et al 109 CA:92663p 1988.
Douvas et al PNAS vol. 88, pp. 6328–6332 1991.

*Primary Examiner*—Russell Travers
*Attorney, Agent, or Firm*—Dara L. Dinner; Stephen Venetianer; Edward T. Lentz

[57] ABSTRACT

Use of a guanine derivative or a prodrug thereof in the treatment of viral infections.

10 Claims, No Drawings

PHARMACEUTICAL TREATMENT

This is a continuation of application Ser. No. 08/380,226, filed Jan. 27, 1995, now abandoned, which is a continuation of application Ser. No. 08/237,936 filed May 2, 1994, now abandoned, which is a continuation of application Ser. No. 07/971,917, filed Jan. 28, 1993, now abandoned.

This invention relates to a method of treatment of HIV-1 infection in humans and animals, and to the use of compounds in the preparation of a medicament for use in the treatment of such infection.

EP-A-141927 (Beecham Group p.l.c.) discloses penciclovir, the compound of formula (A):

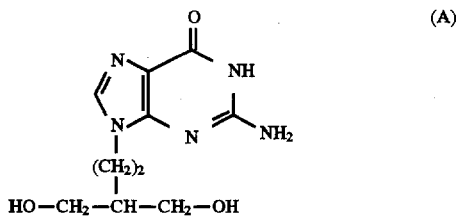

and salts, phosphate esters and acyl derivatives thereof, as antiviral agents. The sodium salt hydrate of penciclovir is disclosed in EP-A-216459 (Beecham Group p.l.c.). Penciclovir and its antiviral activity is also disclosed in Abstract P.V11-5 p.193 of 'Abstracts of 14th Int. Congress of Microbiology', Manchester, England 7–13 Sep., 1986 (Boyd et. al.).

Pro-drugs of the compound of formula (A) are of formula (B):

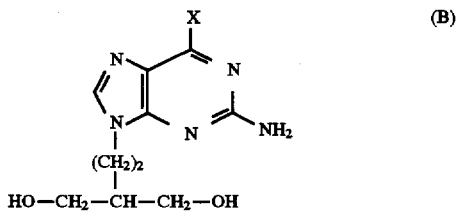

and salts and derivatives thereof as defined under formula (A); wherein X is $C_{1-6}$ alkoxy, $NH_2$ or hydrogen. The compounds of formula (B) wherein X is $C_{1-6}$ alkoxy or $NH_2$ are disclosed in EP-A-141927 and the compounds of formula (B) wherein X is hydrogen, disclosed in EP-A-182024 (Beecham Group p.l.c.) are preferred prodrugs. A particularly preferred example of a compound of formula (B) is that wherein X is hydrogen and wherein the two OH groups are in the form of the acetyl derivative, described in Example 2 of EP-A-182024, hereinafter referred to as famciclovir.

The compounds of formulae (A) and (B) and salts and derivatives thereof have been described as useful in the treatment of infections caused by herpesviruses, such as herpes simplex type 1, herpes simplex type 2, varicella-zoster and Epstein-Barr viruses.

It has now been discovered that these compounds have potential activity against the human immunodeficiency virus (HIV-1), in patients also infected with herpesviruses, and are therefore of potential use in the treatment of HIV infections in such patients.

This discovery is related to the ability of the triphosphate derivative of penciclovir to inhibit the RNA-directed DNA polymerase (reverse transcriptase) activity of human immunodeficiency virus type 1 (HIV-1). The reverse transcriptase of HIV-1 is a virus-encoded enzyme essential for the conversion of genomic RNA into proviral ds-DNA, and is therefore an excellent molecular target for antiviral chemotherapy.

The ability of HIV to enter cells previously infected with herpesviruses is known (for example, B-lymphocytes infected with EBV[1]). The presence of both herpes and human immunodeficiency viruses in the same cell has particular consequences.

1. Penciclovir would be phosphorylated by herpes virus-encoded thymidine kinase leading to a high level of penciclovir triphosphate[2]. The triphosphate formed is not only an inhibitor of herpes DNA polymerase, but this work indicates that it also inhibits HIV reverse transcriptase.

2. HIV replication may be enhanced by herpesvirus transactivating factors. A product of HSV, ICP-4 (infected-cell protein) can increase the initiation of HIV transcription.

3. Double infection of herpesviruses and HIV may result in phenotypic mixing and the production of 'pseudotype' HIV particles bearing herpesvirus envelope glycoproteins[3]. The packaging of HIV genomic RNA with HSV capsid proteins is also believed to occur. Either situation may lead to the infection by HIV of CD4-negative, herpesvirus-permissible cells, previously not susceptible to entry of this virus. This may also result in doubly-infected cells.

Accordingly, the present invention provides a method of treatment of HIV-1 infections in mammals, including humans, which mammals are infected with herpesviruses, which method comprises the administration to the mammal in need of such treatment, an effective amount of a compound of formula (A):

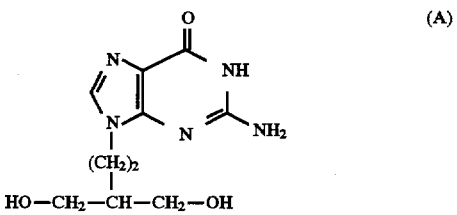

or a pro-drug, or a pharmaceutically acceptable salt, phosphate ester and/or acyl derivative of either of the foregoing.

The term 'acyl derivative' is used herein to include any derivative of the compounds of formula (A) in which one or more acyl groups are present. Such derivatives are included as pro-drugs of the compounds of formula (A) in addition to those derivatives which are per se biologically active.

Examples of pro-drugs, pharmaceutically acceptable salts and derivatives are as described in the aforementioned European Patent references, the subject matter of which are incorporated herein by reference.

A particular pro-drug of interest is 9-(4-acetoxy-3-acetoxymethylbut-1-yl)-2-aminopurine, known as famciclovir.

The compound of formula (A) may also be in one of the forms disclosed in EP-A-216459 (Beecham Group p.l.c.).

The compound of formula (A), pro-drugs, salts and derivatives may be prepared as described in the aforementioned European Patent references.

The compound, in particular, famciclovir, may be administered by the oral route to humans and may be compounded in the form of syrup, tablets or capsule. When in the form of a tablet, any pharmaceutical carrier suitable for formulating such solid compositions may be used, for example magnesium stearate, starch, lactose, glucose, rice, flour and chalk. The compound may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups.

For parenteral administration, fluid unit dose forms are prepared containing the compound and a sterile vehicle. The compound depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

Preferred parenteral formulations include aqueous formulations using sterile water or normal saline, at a pH of around 7.4 or greater, in particular, containing penciclovir sodium salt hydrate.

As is common practice, the compositions will usually be accompanied by written or printed directions for use in the medical treatment concerned.

An amount effective to treat the virus infection depends on the nature and severity of the infection and the weight of the mammal.

A suitable dosage unit might contain from 50 mg to 1 g of active ingredient, for example 100 to 500 mg. Such doses may be administered 1 to 4 times a day or more usually 2 or 3 times a day. The effective dose of compound will, in general, be in the range of from 0.2 to 40 mg per kilogram of body weight per day or, more usually, 10 to 20 mg/kg per day.

The present invention also provides the use of a compound of formula (A) or a pro-drug, or a pharmaceutically acceptable salt, phosphate ester and/or acyl derivative of either of the foregoing, in the preparation of a medicament for use in the treatment of HIV-1 infections in mammals, including humans, which mammals are infected with herpesviruses. Such treatment may be carried out in the manner as hereinbefore described.

The present invention further provides a pharmaceutical composition for use in the treatment of HIV-1 infections in mammals, including humans, which mammals are infected with herpesviruses, which comprises an effective amount of a compound of formula (A) or a pro-drug, or a pharmaceutically acceptable salt, phosphate ester and/or acyl derivative of either of the foregoing, and a pharmaceutically acceptable carrier. Such compositions may be prepared in the manner as hereinafter described.

The compound of formula (A) and its prodrugs show a synergistic antiviral effect in conjunction with interferons; and treatment using combination products comprising these two components for sequential or concomitant administration, by the same or different routes, are therefore within the ambit of the present invention. Such products are described in EP-A-271270 (Beecham Group p.l.c.).

It will be appreciated that the treatment of herpesvirus infected patients may include prophylaxis of herpesvirus episode attacks (suppressive treatment). In patients with HSV infection only, suppressive treatment would probably only be given to those patients with frequent recurrences. In contrast, the aforementioned finding in relation to HIV-1, indicates the need for continuous suppressive treatment with penciclovir to all HIV-1 infected patients with herpesvirus recurrences, particularly HSV-1, HSV-2 and VZV recurrences, even though these recurrences may be infrequent.

The following biochemical data illustrate the invention.

BIOCHEMICAL DATA

Materials and Methods

Chemicals [$^3$H]dGTP (16.3 Ci/mmol) was purchased from Amersham International, Aylesbury, U.K. Template primer Poly (rC). $p(dG)_{12-18}$ (1:1, rC:dG ratio) and 2',3'-dideoxyguanosine-5-triphosphate (ddGTP) were obtained from Pharmacia Ltd., Milton Keynes, U.K. Penciclovir triphosphate (PCV-TP) was prepared in the laboratories of SmithKline Beecham Pharmaceuticals, Great Burgh, United Kingdom.

Reverse transcriptase Purified, *E. coli* expressed HIV-1 reverse transcriptase (RT) was supplied by the Protein Biochemistry Department of SmithKline Beecham Pharmaceuticals, Upper Merion, U.S.A. The enzyme was stored and diluted in a buffer containing 50 mM Tris-HCl (pH 8.0), 10 mM Hepes, 110 mM NaCl, 5.7 mM DTT, 0.3 mM EDTA, 0.06% Triton X-100, 50% glycerol.

Assay for reverse transcriptase activity The reaction mixture for the HIV-1 RT assay contained in a volume of 120 μl: 33 mM Tris HCl (pH 8.0), 100 mM KCl, 3.3 mM $MgCl_2$, 3.3 mM dithiothreitol, 0.2 mM glutathione, 0.33 mM EGTA (ethylene glycol-bis-(β-aminoethyl ether) N,N-tetra acetic acid), 0.033% Triton X-100, 1.02 μM [$^3$H]dGTP, 0–12.39 μM inhibitors ddGTP, PCV-TP, 0.3 $A_{260}$ units/ml Poly (rC). $p(dG)_{12-18}$ and 167 ng/ml RT (equivalent to 2.85 nM for an equimolar mixture of p66 and p51 polypeptides). The reaction mixtures without RT were prepared in the microwells of a 96-well plate and preincubated at 37° C. before the reactions were started by the addition of 20 μl of the enzyme solution. The plates were then incubated for 65 minutes at 37° C. The incorporation rate was linear for the uninhibited control reaction over this time period. The reactions were terminated by the addition of 40 μl of EDTA solution (0.2M, pH7.0). The individual reaction mixtures were transferred to a DEAE filter mat (1205-405, LKB Wallac, Finland), prewetted with 0.3M NaCl/0.03M Na citrate, using a cell harvester (1295-001, LKB Wallac). The filter mat was washed three times in the NaCl/Na citrate buffer and then once in 95% ethanol. Scintillation fluid (Beta Plate Scint, LKB Wallac) was added to the dried filter, and the reaction mixtures assayed for incorporation of radioactive dGMP in an LKB 1205 Beta Plate Liquid Scintillation Counter.

Results

The counts per minute obtained with the uninhibited control reaction mixture, and with a range of concentrations of ddGTP and PCV-TP, are shown in Tables 1 and 2 respectively. From the plots of % inhibition against concentration of inhibitor, approximate $IC_{50}$ values were obtained as follows:

ddGTP: 25 nM (R/S) PCV-TP: 4.3 μM

Conclusion

These results indicate that the concentration of penciclovir triphosphate required to give 50% inhibition of HIV-1 reverse transcriptase is approximately 4 μM. This level of PCV-TP should be obtained in the herpes-infected cell[2].

TABLE 1

Inhibition of HIV-1 Reverse Transcriptase by ddG-Triphosphate

| Concentration of ddGTP (nM) | Incorporation of dGMP (c.p.m.) | % Inhibition |
|---|---|---|
| 0 | 117892 | |
| 1 | 119726 | 0 |
| 10 | 89949 | 23.7 |
| 25 | 58703 | 50.2 |
| 50 | 35091 | 70.2 |
| 75 | 26132 | 77.8 |
| 100 | 22161 | 81.2 |

TABLE 2

Inhibition of HIV-1 Reverse Transcriptase by PCV-Triphosphate

| Concentration of PCV-TP (µM) | Incorporation of dGMP (c.p.m.) | % Inhibition |
|---|---|---|
| 0 | 88892 | |
| 0.124 | 85313 | 4.0 |
| 1.24 | 70061 | 21.2 |
| 3.10 | 51866 | 41.7 |
| 6.19 | 32921 | 63.0 |
| 9.29 | 26436 | 70.3 |
| 12.39 | 23844 | 73.2 |

References

1. Complement Receptor 2 Mediates Enhancement of Human Immunodeficiency virus infection in Epstein-Barr virus-carrying B cells. Tremblay et al., J. Exp. Med. 171, 1791 (1990).
2. Mode of action of 9-(4-hydroxy-3-hydroxymethylbut-1-yl)guanine (BRL 39123) against herpes simplex virus in MRC-5 cells. Vere Hodge and Perkins, A.A.C., 33, 223 (1989).
3. Phenotypic mixing between human immunodeficiency virus and vesicular stomatitis virus or herpes simplex virus. Zhu et al., J. of AIDS, 3, 215 (1990).

We claim:

1. A method of treatment of HIV-1 infections in mammals, which mammals are infected with herpes viruses, which method comprises the administration to the mammal in need of such treatment, an effective amount of a compound of formula (A):

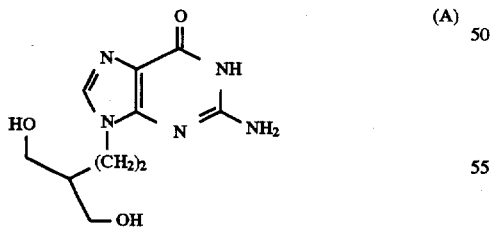

(A)

or a pharmaceutically acceptable salt, phosphate ester and/or acyl derivative of either of the foregoing.

2. A method, according to claim 1, wherein the compound is penciclovir, of formula (A).

3. A method, according to claim 1, wherein the compound is the sodium salt hydrate of the compound of formula (A).

4. A method, according to claim 3 wherein the medicament is in an aqueous formulation, adapted for parenteral administration.

5. A method, according to claim 1, wherein the compound is a pro-drug of the compound of formula (A), of formula (B):

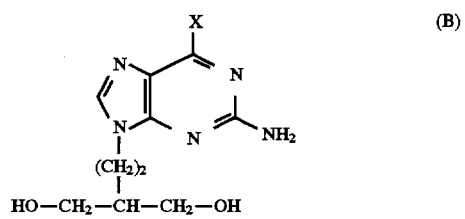

(B)

or a salt or derivative thereof, as defined in respect of formula (A) in claim 1; wherein X is $C_{1-6}$ alkoxy, $NH_2$ or hydrogen.

6. A method, according to claim 5 wherein the pro-drug compound of formula (B) is wherein X is hydrogen, or a derivative thereof, as defined in respect of formula (A) in claim 1.

7. A method, according to claim 6 wherein the pro-drug compound of formula (B) is famciclovir, wherein X is hydrogen and wherein the two OH groups are in the form of the acetyl derivative.

8. A method, according to claim 7 wherein the medicament is adapted for oral administration.

9. A method, according to claim 1, wherein the compound administered is in a 50 mg to 1 g unit dose.

10. A method of treating an HIV patient, which patient has HSV or VZV recurrences, with a continuous suppressive amount of penciclovir, pro-drug of penciclovir or pharmaceutically acceptable salt, phosphate ester and or acyl derivative thereof.

* * * * *